United States Patent [19]

Morimoto et al.

[11] Patent Number: 5,419,912
[45] Date of Patent: May 30, 1995

[54] ADHESIVE PATCH FOR PERCUTANEOUS DELIVERY OF ISOSORBIDE DINITRATE

[75] Inventors: Yasunori Morimoto; Kenji Sugibayashi, both of Sakado; Masatoshi Suzuki, Tokyo, all of Japan

[73] Assignee: Toko Yakuhin Kogyo Co., Ltd., Tokyo, Japan

[21] Appl. No.: 243,005

[22] Filed: May 16, 1994

Related U.S. Application Data

[63] Continuation of Ser. No. 28,225, Mar. 9, 1993, abandoned.

[30] Foreign Application Priority Data

Mar. 26, 1992 [JP] Japan ................... 4-100400

[51] Int. Cl.$^6$ .............................................. A61F 13/00
[52] U.S. Cl. ................... 424/443; 424/448; 514/946; 514/947; 514/969
[58] Field of Search ............. 424/443, 448; 514/946, 514/947, 969

[56] References Cited

U.S. PATENT DOCUMENTS

| | | | |
|---|---|---|---|
| 4,485,087 | 11/1984 | Otsuka | 424/449 |
| 5,176,916 | 1/1993 | Yamanaka | 424/448 |
| 5,204,109 | 4/1993 | Akemi | 424/443 |

FOREIGN PATENT DOCUMENTS

| | | |
|---|---|---|
| 0436203 | 7/1991 | European Pat. Off. . |
| 2497457 | 7/1982 | France . |
| 59-048416 | 3/1984 | Japan . |

OTHER PUBLICATIONS

European Search Report, EP 93 87 0051, May 6th, 1993.

*Primary Examiner*—D. Gabrielle Phelan
*Attorney, Agent, or Firm*—Spencer, Frank & Schneider

[57] ABSTRACT

An adhesive patch for percutaneous delivery of isosorbide dinitrate includes a piece of separating paper; a percutaneous salve preparation which is solvent free and which is comprised of: (a) isosorbide dinitrate; (b) a percutaneous absorption accelerator which is at least one substance selected from the group consisting of a chained monocarboxylate and a higher alcohol; and (c) a tackifier composition as an additive, wherein the chained monocarboxylate is selected from the group consisting of isopropyl palmitate, isopropyl myristate, cetyl lactate, diethyl sebacate, xylol laurate, cetyl isooctanoate and lauryl lactate, wherein the higher alcohol is selected from the group consisting of cetanol, stearyl alcohol, lauryl alcohol, cetostearyl alcohol and myristyl alcohol, and wherein the percutaneous absorption accelerator is present in an amount ranging between 3 and 12 wt % if a chained monocarboxylate is used and between 1 and 3 wt % if a higher alcohol is used; and a surface coating material which is polymeric.

5 Claims, No Drawings

ADHESIVE PATCH FOR PERCUTANEOUS DELIVERY OF ISOSORBIDE DINITRATE

This application is a Continuation of application Ser. No. 08/028,225, filed Mar. 9, 1993, now abandoned.

BACKGROUND OF THE INVENTION

1. Applicable Field of Industry

This invention relates to a percutaneous salve preparation in the form of an adhesive tape to be applied to the surface of the skin so as to continuously administer isosorbide dinitrate ($C_6H_8N_2O_8$: 236.14) having an anti-angina pectoris effect to the living body via the skin surface.

2. Related Art

Isosorbide dinitrate (hereinafter referred to as ISDN) has been widely used in the form of sublingual and oral tablets as a medicine effective to prevent and suppress senile angina pectoris, angina pectoris produced as a result of myocardial infarction and coronary arteriosclerosis. However, a percutaneous salve preparation in the form of an adhesive tape is gaining popularity as means for administering ISDN to the living body because it is free from the first-pass effect of ISDN in the liver unlike an oral agent and maintains the serum concentration of ISDN to an effective level for a prolonged period of time (24 to 48 hours).

A conventional technique of producing a percutaneous salve preparation in the form of an adhesive tape consists in causing ISDN molecules to coexist with ISDN crystals in an acrylic adhesive layer so that the ISDN crystals may operate as a whole as a reservoir for supplying ISDN molecules to fill the place of those absorbed by the living body through the skin to which the preparation is applied so that ISDN molecules may be transferred from the tape to the skin surface at a given rate to maintain the concentration of dissolved ISDN on the skin surface to a constant level.

PROBLEMS TO BE SOLVED BY THE INVENTION

While a known percutaneous salve preparation in the form an adhesive tape can be percutaneously absorbed by the living body at a given rate, the rate of percutaneous absorption is rather poor because it does not contain any percutaneous absorption accelerator. It is also accompanied by a safety problem because it can irritate the skin unlike a conventional ointment.

The above identified problems can be very severe because a percutaneous salve preparation in the form of an adhesive tape is normally held on the skin for approximately 48 hours. Since skin irritation can be alleviated to some extent by reducing the size of a patch of the preparation to be applied to the skin surface, there has been proposed a percutaneous salve preparation in the form of an adhesive tape having a surface area of a half of a normal patch (approximately 50 cm$^2$) in an attempt to bypass the problem.

However, such a proposed patch is still not completely free from the problem of skin irritation. If the surface area of such a patch is reduced still further, the rate of percutaneous supply of ISDN will be undesirably reduced and the serum concentration of ISDN in the subject cannot be maintained to an effective level.

OBJECT OF THE INVENTION

In view of the above identified problems of a conventional percutaneous salve preparation, it is therefore an object of the present invention to provide a percutaneous salve preparation in the form of a patch that can ensure an enhanced level of percutaneous absorption of ISDN with a reduced surface area of the patch and therefore overcome the above problems of a conventional percutaneous salve preparation.

SUMMARY OF THE INVENTION

According to the invention, the above object is achieved by providing a percutaneous salve preparation in the form of a patch comprising isosorbide dinitrate, a chained monocarboxylate and/or a higher alcohol as a percutaneous absorption accelerator and a tackifier.

The percutaneous absorption accelerator to be added to the preparation can be selected from isopropyl palmitate, isopropyl myristate, cetyl lactate, diethyl sebacate, xylol laurate, cetyl isooctanoate and lauryl lactate if a chained monocarboxylate is used and/or from cetanol, stearyl alcohol, lauryl alcohol, cetostearyl alcohol and myristyl alcohol if a higher alcohol is used. An appropriate combination of any of above listed percutaneous absorption accelerators can show an enhanced percutaneous absorption effected.

Any tackifier may be used for the purpose of the present invention as long as it can be normally applied to the skin without irritation, although the use of a styrene-isoprene-styrene block copolymer to which an ordinary tackifier and a plasticizer are added along with a filler and/or an antioxidant, if desired, may be a recommended choice because the tackiness and the cohesion of a percutaneous absorption accelerator added salve preparation can be adequately controlled by a rubber type tackifier.

The content of a chained monocarboxylate in a percutaneous salve preparation according to the invention is preferably between 3 and 12 wt %, whereas that of a higher alcohol is preferably between 1 and 3 wt %.

A percutaneous absorption accelerator to be used for a percutaneous salve preparation in the form of a patch according to the invention produces a sustained effect of causing the ISDN in the preparation to be absorbed via the skin surface of a living body and maintain the serum concentration of ISDN to a desired level for a prolonged period of time.

BEST MODES OF CARRYING OUT THE INVENTION

A number of examples having compositions as illustrated in Table 1 below were prepared by using, in each example, a rubber-type tackifier (containing a styrene-isoprene-styrene block copolymer by 35 wt %, resin by 50 wt % and fluid paraffin by 15 wt %), a silicon-type tackifier (available from Dow Corning under the tradename of BIO-PSA Q7-2920) or an acryl-type tackifier (MS-1), to which a given amount of a percutaneous absorption accelerator selected from isopropyl myristate (hereinafter referred to as IPM), lauryl lactate (hereinafter referred to as LL), lauryl alcohol (hereinafter referred to as LA) and myristyl alcohol (hereinafter referred to as MA) was added along with a 20 wt % of ISDN and an appropriate solvent such as ethyl acetate to produce an even solution. Each of the prepared solutions was then applied to a piece of separating paper to a thickness of approximately 4 mg/cm$^2$ and then the solvent was removed from the mixtures. Thereafter, the surface of the mixture was covered with a surface coating material (a laminate comprising a 6 μm thick polyester film layer and a 17 μm thick ethylenevinylacetate (EVA) film) to produce a specimen.

TABLE 1

Compositions of the Specimens (unit = wt %)

| | rubber/ silicon/acryl | tackifier percutaneous accelerator IMP | tackifier percutaneous accelerator LL | absorption LA | absorption MA | medicine ISDN |
|---|---|---|---|---|---|---|
| comparative example 1 | 80 | | | | | 20 |
| comparative example 2 | | 80 | | | | 20 |
| comparative example 3 | | | 80 | | | 20 |
| example 1 | 68 | 12 | | | | 20 |
| example 2 | 75 | | 5 | | | 20 |
| example 3 | 77 | | | 3 | | 20 |
| example 4 | 76.5 | | | | 3.5 | 20 |
| example 5 | | 75 | 5 | | | 20 |
| example 6 | | 75 | | 5 | | 20 |
| example 7 | | 77 | | 3 | | 20 |
| example 8 | | 76.5 | | | 3.5 | 20 |
| example 9 | | | 75 | 5 | | 20 |
| example 10 | | | 75 | | 5 | 20 |
| example 11 | | | 77 | 3 | | 20 |
| example 12 | | | 76.5 | | 3.5 | 20 |
| example 13 | 76 | 3 | | 1 | | 20 |
| example 14 | 71 | 6 | | 3 | | 20 |
| example 15 | 68 | 9 | | 3 | | 20 |

TABLE 1-continued

Compositions of the Specimens (unit = wt %)

| | rubber/ silicon/acryl | tackifier percutaneous accelerator IMP | tackifier percutaneous accelerator LL | absorption LA | absorption MA | medicine ISDN |
|---|---|---|---|---|---|---|
| marketed article | 80 | | | | | 20 |

Then, the specimens were subjected to a series of tests as described below to obtain the respective results as listed in Tables 2 through 5 below.

TESTS (1) Percutaneous Permeation Test

A two-chamber type diffusion cell using a piece of skin of a hairless rat cut from the abdomen was used to test the percutaneous permeation of the specimens.

(2) Tackiness Test

Each of the specimens was applied to the surface of a bakelite plate, which was then pressed by a rubber roller having a weight of 2 kg as the roller was reciprocally moved on the plate for three times. 20 minutes thereafter, the specimen was peeled at a rate of 300 mm/min. by holding it to an angle of 180° to determine the anti-peeling strength of the specimen. The test was conducted at a temperature of 23° C. and a relative humidity of 65%. The Results of the Percutaneous Permeation Test

TABLE 2

Percutaneous Permeation Effect of Rubber-Type Tackifiers Added to Respective Percutaneous Absorption Accelerators on Rat's Cut Skin (unit = μg/cm²)

| time | comparative example 1 blank | example 1 IPM 12 wt % | example 2 LL wt 5% | example 3 LA 3 wt % | example 4 MA 3.5 wt % |
|---|---|---|---|---|---|
| 1 | 11.8 | 38.9 | 15.4 | 20.6 | 9.9 |
| 2 | 30.5 | 92.9 | 38.1 | 65.8 | 22.6 |
| 4 | 74.4 | 230.4 | 82.4 | 131.5 | 71.8 |
| 6 | 133.5 | 340.8 | 176.2 | 207.0 | 123.4 |
| 8 | 179.9 | 436.2 | 255.7 | 301.5 | 190.5 |
| 10 | 256.6 | 556.3 | 330.0 | 401.2 | 242.3 |
| 24 | 590.5 | 1034.2 | 792.7 | 847.6 | 914.2 |

TABLE 3

Percutaneous Permeation Effect of Silicon-Type Tackifiers Added to Respective Percutaneous Absorption Accelerators on Rat's Cut Skin (unit = μg/cm²)

| time | comparative example 2 blank | example 5 IPM 5 wt % | example 6 LL 5 wt % | example 7 La 3 wt % | example 8 MA 3.5 wt % |
|---|---|---|---|---|---|
| 1 | 3.9 | 35.4 | 14.2 | 27.4 | 17.5 |
| 2 | 16.2 | 103.3 | 22.1 | 65.7 | 54.6 |
| 4 | 42.6 | 186.9 | 61.3 | 170.5 | 118.2 |
| 6 | 83.5 | 270.5 | 114.6 | 270.1 | 190.6 |
| 8 | 136.2 | 372.0 | 190.2 | 378.7 | 265.4 |
| 10 | 177.5 | 487.7 | 253.9 | 484.5 | 352.8 |
| 24 | 582.6 | 983.5 | 822.8 | 851.9 | 795.0 |

TABLE 4

Percutaneous Permeation Effect of Acryl-Type Tackifiers Added to
Respective Percutaneous Absorption Accelerators on Rat's Cut Skin (unit = µg/cm²)

| time | comparative example 3 blank | example 9 IPM 5 wt % | example 10 LL 5 wt % | example 11 LA 3 wt % | example 12 MA 3.5 wt % | marketed article |
|---|---|---|---|---|---|---|
| 1  | 16.5  | 70.6  | 20.9  | 40.2  | 44.2  | 12.4  |
| 2  | 48.1  | 152.5 | 60.0  | 82.5  | 87.4  | 39.3  |
| 4  | 120.4 | 241.1 | 140.9 | 180.5 | 201.6 | 101.4 |
| 6  | 179.5 | 340.6 | 220.1 | 267.9 | 292.6 | 161.9 |
| 8  | 243.1 | 449.8 | 295.6 | 351.4 | 387.1 | 221.5 |
| 10 | 293.6 | 520.1 | 365.4 | 440.5 | 491.3 | 290.4 |
| 24 | 586.4 | 746.8 | 727.6 | 721.4 | 728.8 | 576.0 |

TABLE 5

Percutaneous Permeation Effect of (Combined) Rubber-Type
Tackifiers Added to Respective Percutaneous Absorption
Accelerators on Rat's Cut Skin (unit = µg/cm²)

| time | example 13 IPM 3 wt % LA 1 wt % | example 14 IPM 6 wt % LA 3 wt % | example 15 IPM 9 wt % LA 3 wt % |
|---|---|---|---|
| 1  | 15.5  | 13.7  | 23.9   |
| 2  | 34.6  | 38.5  | 62.9   |
| 4  | 49.2  | 85.4  | 148.4  |
| 6  | 125.8 | 137.7 | 233.8  |
| 8  | 176.1 | 204.5 | 348.5  |
| 10 | 230.7 | 274.4 | 439.9  |
| 24 | 715.4 | 814.9 | 1202.8 |

All the specimens containing one or more than one tackifier and a percutaneous absorption accelerator according to the present invention proved to be more excellent and advantageous in terms of percutaneous absorption and showed a rate of absorption approximately 1.2 to 1.7 times higher than that of the specimens containing no such additives.

It was also provided that the specimens containing more than one percutaneous absorption accelerators were still more excellent in terms of percutaneous absorption.

THE RESULTS OF THE TACKINESS TEST

The results of the tackiness test proved that the use of an acryl-type or silicon-type tackifier added to a percutaneous absorption accelerator can remarkably reduce the tackiness of the product but the tackiness can be recovered by controlling the ratio of the tackifier to the percutaneous absorption accelerator. The tackiness of a percutaneous salve preparation according to the invention and containing a rubber-type tackifier can be improved by controlling the ratio of the rubber-type tackifier to the fluid paraffin contained in the preparation as a general plasticizer and the percutaneous absorption accelerator also contained in the preparation or by adjusting the content of the rubber and that of the percutaneous absorption accelerator.

TABLE 6

The Results of a Tackiness Test (unit = g/20 mm)

| rubber-type | tackifier | silicon-type | tackifier | acryl-type | tackifier |
|---|---|---|---|---|---|
| comparative example 1 | 900 | comparative example 2 | 1100 | comparative example 3 | 810 |
| example 1 | 750 | example 5 | 810  | example 9  | 1000 |
| example 2 | 950 | example 6 | 970  | example 10 | 1030 |
| example 3 | 970 | example 7 | 1400 | example 11 | 1300 |
| example 4 | 850 | example 8 | 1500 | example 12 | 1300 |
|           |     |           |      | marketed article | 610 |
| example 13 | 800 | | | | |
| example 14 | 680 | | | | |
| example 15 | 770 | | | | |

EFFECTS

As is apparent from the above description, a percutaneous salve preparation according to the invention and containing ISDN is much more excellent than any comparable existing preparations in terms of percutaneous absorption and tackiness.

What is claimed is:

1. An adhesive patch for percutaneous delivery of isosorbide dinitrate, comprising:
   a sheet of paper;
   a percutaneous salve preparation which is applied to the sheet of paper, which consists of:
   (a) isosorbide dinitrate;
   (b) a percutaneous absorption accelerator which is at least one substance selected from the group consisting of a chained monocarboxylate and a higher alcohol;
   (c) a tackifier composition as an additive,
   wherein the chained monocarboxylate is selected from the group consisting of isopropyl palmitate, isopropyl myristate, cetyl lactate, diethyl sebacate, xylol laurate, cetyl isooctanoate and lauryl lactate;
   (d) a fluid paraffin softening agent;
   (e) at least one filler; and
   (f) at least one stabilizer,
   wherein the higher alcohol is selected from the group consisting of cetanol, stearyl alcohol, lauryl alcohol, cetostearyl alcohol and myristyl alcohol, and
   wherein the percutaneous absorption accelerator is present in an amount ranging between 3 and 12 wt % if a chained monocarboxylate is used and between 1 and 3 wt % if a higher alcohol is used; and
   a polymeric sheet which covers the percutaneous salve preparation and which is removable when the adhesive patch is used.

2. The percutaneous salve preparation according to claim 1, wherein the percutaneous absorption accelerator is isopropyl myristate and lauryl alcohol.

3. The adhesive patch according to claim 1, wherein the tackifier composition is comprised of a styrene-isoprene-styrene block copolymer.

4. The adhesive patch according to claim 1, wherein the polymeric sheet is a laminate of a layer of polyester and a layer of ethylene-vinylacetate copolymer.

5. An adhesive patch for percutaneous delivery of isosorbide dinitrate, comprising:
   a sheet of paper;
   a percutaneous salve preparation which is applied to the sheet of paper, which consists of:
   (a) isosorbide dinitrate;
   (b) a percutaneous absorption accelerator which is at least one substance selected from the group consisting of a chained monocarboxylate and a higher alcohol;
   (c) a tackifier composition as an additive,
   wherein the chained monocarboxylate is selected from the group consisting of isopropyl palmitate, isopropyl myristate, cetyl lactate, diethyl sebacate, xylol laurate, cetyl isooctanoate and lauryl lactate;
   (d) a fluid paraffin softening agent;
   (e) at least one filler; and
   (f) at least one stabilizer,
   wherein the higher alcohol is selected from the group consisting of cetanol, stearyl alcohol, lauryl alcohol, cetostearyl alcohol and myristyl alcohol, and
   wherein the percutaneous absorption accelerator is present in an amount ranging between 3 and 12 wt % if a chained monocarboxylate is used and between 1 and 3 wt % if a higher alcohol is used; and
   a polymeric sheet which covers the percutaneous salve preparation and which is removable when the adhesive patch is used, prepared by a process comprising:
   preparing a solution of isosorbide dinitrate, the percutaneous absorption accelerator, and the tackifier composition in a solvent;
   applying the solution to the sheet of paper;
   removing the solvent to provide the percutaneous salve preparation; and
   covering the percutaneous salve preparation with the polymeric sheet.

* * * * *